United States Patent [19]

Nathanson

[11] Patent Number: 4,883,801

[45] Date of Patent: Nov. 28, 1989

[54] XANTHINE DERIVATIVE PEST CONTROL AGENTS

[75] Inventor: James A. Nathanson, Wellesley, Mass.

[73] Assignee: The General Hospital Corporation, Boston, Mass.

[21] Appl. No.: 898,748

[22] Filed: Aug. 18, 1986

Related U.S. Application Data

[63] Continuation-in-part of Ser. No. 648,086, Sep. 7, 1984, abandoned.

[51] Int. Cl.$^4$ .............................................. A01N 43/90
[52] U.S. Cl. ...................................... 514/263; 514/265
[58] Field of Search ................................ 514/263, 265

[56] References Cited

U.S. PATENT DOCUMENTS

| | | | | |
|---|---|---|---|---|
| 1,653,710 | 12/1927 | Kitchen | ............................ | 424/195.1 |
| 2,362,614 | 11/1944 | Calwa | ............................ | 514/612 |
| 3,663,692 | 5/1972 | Kare | .................................. | 424/253 |

OTHER PUBLICATIONS

King, *Chemicals Evaluated as Insecticides and Repellents*, pp. 1–21, 100–101 and 322–323 (1954).
Moffett, et al., *Comp. Biochem. Physiol.*, vol. 75C, pp. 305–310, 1983.
Janzen, et al., *Phytochem.*, vol. 16, pp. 223–227 (1977).
Clark, *Ent. Exp. & Appl.*, vol. 29, pp. 189–197 (1981).
McDaniel, et al., *J. Insect Physiol.*, vol. 20, pp. 245–252 (1974).
Targa, et al., *Brazil J. Genetics*, vol. 4, pp. 669–677 (1982).
Srinivasan et al., *J. Toxicol. & Envir. Health*, vol. 2, pp. 569–576 (1977).
Srinivasan et al., *Toxicology Letters*, vol. 3, pp. 229–232 (1979).
Srinivasan et al., *Toxicology Letters*, vol. 3, pp. 101–105 (1979).
Sittig, *Pesticide Mfg. & Toxic Mat'ls. Control Encyclopedia*, pp. 1–10 (1980).
Pojakovick et al., *Pesticide Biochem. and Physiology*, vol. 6, pp. 10–19 (1976).

*Primary Examiner*—Douglas W. Robinson
*Assistant Examiner*—Zohreh A. Fay
*Attorney, Agent, or Firm*—Saidman, Sterne, Kessler & Goldstein

[57] ABSTRACT

The use of xanthine derivatives having the general formula:

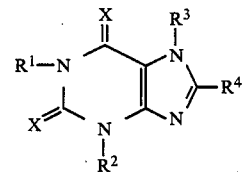

or

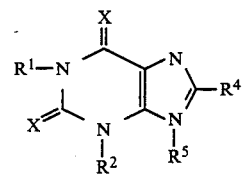

as pesticidal and pestistatic agents is disclosed, as well as pesticidal and pestistatic compositions containing same.

18 Claims, 2 Drawing Sheets

XANTHINE DERIVATIVE PEST CONTROL AGENTS

CROSS-REFERENCE TO RELATED APPLICATIONS

This is a continuation-in-part of U.S. application Ser. No. 648,086 filed Sept. 25, 1984, now abandoned, all subject matter of which is herein incorporated by reference.

BACKGROUND OF THE INVENTION

1. Field of the Invention

The present invention is directed to a method for controlling a pest comprising bringing into contact with the pest a pest-controlling amount of a compound from the group comprising derivatives of xanthine.

2. Description of the Background Art

Despite the recent development and great promise of such advanced pest-controlling compositions as chemical sterilants, pheromones or ecologically-based insect control strategies, it is doubtless that, at present, the use of chemical pesticides still plays a predominant role. The use of insecticides often represents the difference between profitable crop production for farmers and no marketable crop at all, and the value of insecticides in controlling human and animal diseases has been dramatic.

Therefore, in parallel to the aforementioned newer technologies for pest control, there has been active research and investigation into the detailed biochemical modes of action of existing known chemical pesticides. Thus, for example, Nathanson, et al., *Molecular Pharmacology*, 20: 68–75 (1981), presented evidence indicating that the formamidine pesticides chlordimeform (CDM) and N-demethylchlordimeform (DCDM) may affect octopaminergic neurotransmission. CDM and DCDM have been reported to mimic the effects of octopamine in stimulating light emission in the firefly lantern (Hollingworth, R. M., et al., *Science*, 208: 74–76 (1982)) and in effecting nerve-evoked muscle responses in the locust leg (Evans, P. D., *Nature*, 287: 60–62 (1980)). Nathanson, et al., supra, found that DCDM, which is the probable in vivo metabolite of CDM is about six-fold more potent than octopamine itself as a partial agonist of light organ octopamine-stimulated adenylate cyclase. Stimulation by the formamidines resulted in increased formation of the intracellular messenger, cyclic AMP (cAMP). This stimulation was blocked by cyproheptadine, clozapine, fluphenazine and phentolamine compounds, also known to block the octopamine receptor. Nathanson, et al., concluded that DCDM is the most potent octopaminergic compound described.

Similar results were observed by Hollingworth, et al. (reported in the *Scientific Papers of the Institute of Organic and Physical Chemistry of Wroclaw Technical University*, No. 22, Conference 7 (1980)). These authors demonstrated that certain formamidines act on octopamine receptors to induce the synthesis of cyclic AMP, and that this response is blocked by both phentolamine and cyproheptadine, which are known to act as octopaminergic antagonists in insects. The authors also suggested that these formamidines are potent stimulators of the octopamine sensitive adenylate cyclases in the thoraxic ganglia of *Periplaneta americana*, and in the ventral nerve cord and fat body of *M. sexta*. The authors suggest that the stimulation of octopamine receptors underlies a number of toxic responses seen with formamidines on insects.

It should be noted that the presence of an insect adenylate cyclase enzyme which is sensitive to naturally occurring D(−)octopamine as a "neuro transmitter" has been known for some time (Nathanson, et al., *Science* 180: 308–310 (1973) (cockroach); Nathanson, *Ibid*, 203: 65–68 (1979) (firefly); Evans, J., *Neurochem.*, 30: 1015–1022 (1978) (cockroach)).

The study of cyclic AMP as a "second messenger" has led to the accepted model that a hormone or neuro transmitter binds at a cell-membrane bound receptor, which activates adenylate cyclase to a form capable of converting ATP in the cytoplasm of the cell into cAMP. cAMP then relays the signal brought by the hormone or neuro transmitter from the membrane to the interior of the cell. Agonists of the hormone or neuro transmitter are, by definition, capable of eliciting the same response (see, for example, Nathanson and Greengard, *Scientific American*, 237: 108–119 (1977)). Among other actions, cAMP stimulates the conversion of inactive phosphorylase b into phosphorylase a, a reaction catalysed by phosphorylase kinase. This reaction is, in turn, catalysed by an enzyme, now called protein kinase, which occurs in an inactive and active form. Its active form catalyses the phosphorylation of inactive phosphorylase kinase by ATP to yield the active phosphorylated form by a reaction in which ATP is the phosphate-group donor.

Protein kinase, the key enzyme in linking cAMP to the phosphorylase system and to other cyclic AMP-regulated processes, is an allosteric enzyme, i.e., an enzyme whose reactivity with another molecule is altered by combination with a third molecule that is not a substrate. Its inactive form contains two types of subunits, a catalytic (C) subunit and a regulatory (R) subunit which inhibits the catalytic subunit. cAMP is the allosteric modulator of protein kinase, binding to a specific site on the regulatory subunit and causing the inactive CR complex to dissociate, yielding R-cAMP complex, and the free C subunit, which is now catalytically active. Thus, cAMP removes the inhibition of enzyme activity that is imposed by the binding of the regulatory subunit (Lehninger, *Biochemistry*, 2nd Ed., pp. 812–813).

The enzyme responsible for the destruction of cAMP is phosphodiesterase, which catalyzes the hydrolytic reaction as follows:

$$cAMP + H_2O \xrightarrow{phosphodiesterase} adenosine\ 5'\text{-phosphate}.$$

It is known that phosphodiesterase activity is inhibited by caffeine and theophylline, alkaloids present in small amounts in coffee and tea. Both caffeine and theophylline have long been known to prolong or intensify the activity of epinephrine, presumably due to increased persistence of cAMP in cells stimulated by epinephrine.

Rojakovick, A. S., et al., *Pesticide Biochemistry and Physiology*, 6:10–19 (1976), explored the interaction between insecticidal activity and cAMP as a secondary messenger, surveying the direct effects of a variety of different types of insecticides upon the activities of adenylate cyclase and phosphodiesterase. The survey of the direct effects of TEPP, methylparaoxon, DDT, Dieldrin, Aldicarb, Dimetilan, Rotenone, Allethrin, and Oxythioquinox upon cockroach brain adenylate cyclase in vitro led the authors to the conclusion that the compounds have essentially no direct effects on adenylate cyclase in vitro. The same nine insecticides were also evaluated for their effect upon cockroach brain phosphodiesterase in vitro. Certain of the compounds showed a general relationship of increasing inhibition with increasing concentration of insecticide, while DDT and Dieldrin appeared to be activators of phosphodiesterase. Oxythioquinox proved to be the most potent inhibitor of cockroach brain phosphodiesterase, giving over 80% inhibition. By comparison, using identical assay techniques, 1,000-fold greater concentrations of aminophylline and theophylline, the most widely used phosphodiesterase inhibitors in adenylate cyclase assays, inhibited 83.2 and 73.8%, respectively. The authors concluded that, while Oxythioquinox and other quinoxoline dithiol derivatives were demonstrated to be potent in vitro inhibitors of phosphodiesterases, no direct relationship of this activity to their mode of toxic action could be determined. Finally, the authors concluded that the broad distribution of phosphodiesterases in the animal kingdom makes it unlikely that phosphodiesterase inhibition is a direct cause of the selective acaricidal activity of the compounds.

Calva, U.S. Pat. No. 2,362,614, describes fluorine-containing insecticides. Disclosed are the hydrofluoric acid addition compounds of ammonia-substituted compounds giving rise to primary, secondary or tertiary amines and polyamines. Insecticidal activity is described as derived from the direct combination of the fluorine-nitrogen link. Caffeine is included in the patent disclosure among the "alkylamines with or without substituent groups."

French Pat. No. 2,138,186 to Aries discloses insecticidal compositions of urinylphosphate esters which are stabilized by purine derivatives. Included among the purine derivatives are purines substituted in the 2, 4 and 8 positions. No insecticidal activity, however, is attributed to the purine compounds, the compounds performing the function of stabilizing the active phosphorus compounds.

Rizvi, S. J. H., et al., *Indian J. Exp. Biol.*, 18: 777-8 (1980), explored the herbicidal activity of ethanolic extracts of leaves and seeds of 49 different plants. The seed extract of *Coffea arabica* proved most potent. Fractionation of the extract of *Coffea arabica* in different organic solvents produced a variety of fractions, all of which were tested for the desired activity. The chloroform fraction completely inhibited the seed germination of the test weed at 5,000 ppm. The authors suggested *Coffea arabica* as a possible source of natural herbicide. The same authors, in *Agra. Biol. Chem.*, 45 (5): 1255-1256 (1981), identified the active weedicidal ingredient as 1,3,7-trimethylxanthine (caffeine). No insecticidal activity for caffeine, however, was disclosed. Rizvi, S. J. H., et al., *Journal of Applied Entomology*, Vol. 90, No. 4, pp. 378-381 (1980), studied the 1,3,7-trimethyl-xanthine isolate of *Coffea arabica* and found it to be effective as a chemosterilant for *Callosobrucaus chinensis*, causing nearly 100% sterility at a concentration of 1.5%. No suggestion of utility as a pesticidal agent was disclosed.

Given the continuous need for increased selectivity and effectiveness in pest control agents, it became desirable that pesticidal and pestistatic agents from naturally occurring products be developed. Although certain fluorinated amines, including fluorinated caffeine, have been suggested as pesticides (Calva, supra), and although other xanthine derivatives unsubstituted in the 1, 3, and 7 position (the hypoxyxanthines of Aries, supra) have been suggested as stabilizers for phosphate insecticides, and although caffeine has been suggested as a chemisterilant (Rizvi et al., supra), the pesticidal and pestistatic action of substituted xanthine derivatives has not been known prior to this invention.

SUMMARY OF THE INVENTION

The xanthine derivatives, including caffeine and theophylline, are found in berries, seeds, and leaves of a number of species, including tea, coffee, cocoa and cola. Although methylxanthines are one of the most frequently used stimulants employed by the human population, their natural function in plants was not known up to the present. It is known, however, that to discourage insect feeding, many plants have evolved endogenous chemical defenses, ranging from specific toxins and substances with pheromone-like activity to less specific bitter-tasting aversive substances.

Based on observations by this inventor and others that the mode of action of certain formamidine pesticides was through their octopaminergic agonist activity on octopamine receptors present in the pest, and that these pest control agents were acting through generation of cAMP as a "second messenger," the inventor then observed that the effectiveness of octopaminergic agonist pest control agents could be greatly enhanced when the quantity and half-life of generated cAMP was augmented by inhibiting insect phosphodiesterase enzymes, which are capable of hydrolyzing cAMP. This observation, coupled with the known phosphodiesterase-inhibiting activity of the methylxanthines, led to the discovery of the invention embodied in applicant's commonly assigned co-pending application Serial No. 605,845, filed May 1, 1984, incorporated by reference herein.

Recognizing the critical role that the phosphodiesterase inhibitors played in the enhancement of octopaminergic agonist pest control agents, the present inventor then began to explore the possibility of the use of certain phosphodiesterase inhibitors alone.

Initially, coffee and tea were investigated for pestistatic or pesticidal activity. The results of these experiments, reported below at Example 1, suggested that pesticidal and pestistatic activity existed for the coffee or tea.

To investigate the possible contribution of endogenous xanthine derivatives to the pesticidal activity described above, the action of purified xanthine derivatives on insects, including Manduca larvae, was examined. The results of one such experiment are reported below at Example 2, as well as the method of investigation. Based on the results of Example 2, it appeared that endogenous xanthine derivatives had pesticidal activity.

Endowed with this knowledge, the inventor then set out to explore the pesticidal and pestistatic activities of various xanthine derivatives, leading to the present invention. The inventor discovered that certain xanthine derivatives possess the ability to inhibit phosphodiesterase activity, and that this ability correlates directly with the invertebrate pest-controlling characteristics of the compound. Thus, as a result of the present invention, it is possible to quickly and routinely evaluate, in vitro, potentially active compounds based on their ability to inhibit phosphodiesterase activity. Thus, this invention comprises a method of pest control comprising bringing into contact with said pest a pest-controlling amount of an agent consisting essentially of a compound having the general formula (I) or (II):

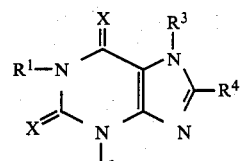

(I)

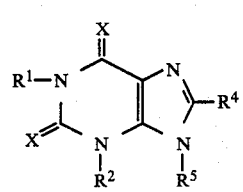

(II)

wherein:

X is oxygen or sulfur;

$R^1$, $R^2$, $R^3$, $R^4$ and $R^5$ are selected from hydrogen; aliphatic hydrocarbons having 1-8 carbon atoms; cycloaliphatic hydrocarbons having 3-8 carbon atoms; substituted aliphatic hydrocarbons having 1-8 carbon atoms and cycloaliphatic hydrocarbons having 3-8 carbon atoms, substituted with 1-3 halogen atoms, $C_1$-$C_4$ alkyl, or hydroxy; alkoxy having 1-6 carbon atoms; phenyl; naphthyl; halo, hydroxy, or $C_1$-$C_4$ alkyl-substituted phenyl or naphthyl; phenoxy; substituted phenoxy; and the like, and acid addition salts thereof, and further, wherein at least one of $R^1$, $R^2$, $R^3$, or $R^5$ is other than hydrogen. For compound I, $R^1$, $R^2$, and $R^3$ are not each methyl simultaneously.

The inventor has found that on the basis of structure alone it is not possible to predict which xanthine derivatives will have pesticidal activity. These findings are shown in Examples 15-47. Therefore, as mentioned above, part of the inventor's discovery involved the development of a procedure to determine, on the basis of their ability to inhibit phosphodiesterase, which compounds have pesticidal activity.

Therefore the most preferred compounds are defined as having a $K_i$ for inhibiting phosphodiesterase of not more than 0.1, where $K_i$ is defined as the concentration in millimoles/liter of the xanthine derivative required to produce a 50% in vitro inhibition of the phosphodiesterase activity in tobacco hornworm nerve cord, using the conditions described.

Such agents are further defined, in vivo, as having a $V_{max}$ of more than 50%, where $V_{max}$ is expressed as the inhibition of feeding at the highest dose used, usually a 3% spray solution, and an $EC_{50}$ of less than 3% (gm/100 ml), $EC_{50}$ being the spray concentration required to cause 50% inhibition of feeding, as calculated from dose-response curves.

As described in Example 47, using the in vitro test, it is possible to distinguish phosphodiesterase inhibiting active or inactive compounds that are structurally similar.

DESCRIPTION OF THE PREFERRED EMBODIMENTS

Figure 1C:
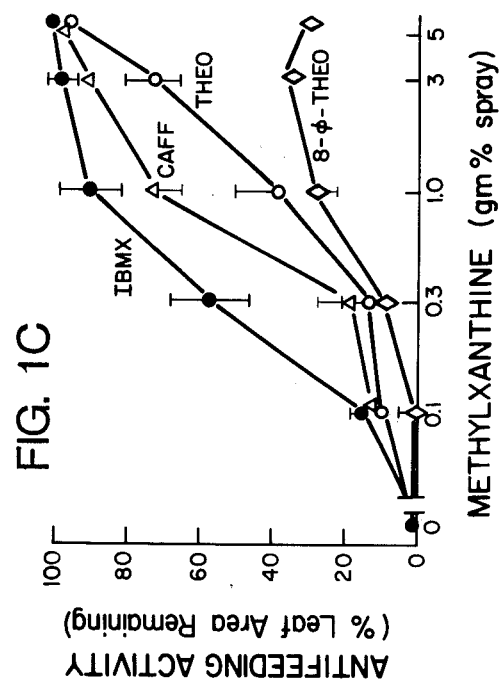
FIG. 1C is a graph quantitating the antifeeding effect of xanthine derivatives applied as a spray to tomato leaves subsequently exposed to tobacco hornworm larvae for 4 days.

By the terms "pest-controlling" or "pest-controlling activity," used throughout the specification and claims, are meant to include any pesticidal (killing) or pestistatic (inhibiting, maiming or generally interfering) activities of a composition against a given pest. Thus, these terms not only include killing, but also include such activities as those of chemisterilants which produce sterility in insects by preventing the production of ova or sperm, by causing death of sperm or ova, or by producing severe injury to the genetic material of sperm or ova, so that the larvae that are produced do not develop into mature progeny.

By the term "inhibiting the feeding" is meant to include both pesticidal activity wherein the pest is killed by the compound, as well as the situation wherein the feeding activity of the larvae is substantially affected and limited.

By the term "pest" is meant any phosphodiester-ase-containing invertebrate. These pests include, but are not limited to, round worms (e.g., hookworms, trichina, and ascaris); flat worms (e.g., liver flukes and tapeworms); jointed worms (e.g., leeches); molluscs (e.g., parasitic snails); and arthropods (insects, spiders, centipedes, millipedes, crustaceans (e.g., barnacles)). In particular, included among the arthropods are ticks, mites (both plant and animal), lepidoptera (butterflies and moths and their larvae), hemiptera (bugs), homoptera (aphids, scales), and coleopera (beetles). Also included are spiders, anoplura (lice), diptera (flies and mosquitos), tricoptera, orthoptera (e.g., roaches), odonta, thysanura (e.g., silverfish), collembola (e.g., fleas), dermaptera (earwigs), isoptera (termites), ephemerids (mayflies), plecoptera, malophaga (biting lice), thysanoptera, and siphonaptera (dictyoptera, psocoptera, and certain hymenoptera (e.g., those whose larvae feed on leaves)). By the term "xanthine derivative" or "methyl xanthine derivatives" are meant compounds having the general formula (I) or (II):

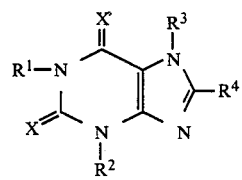

(I)

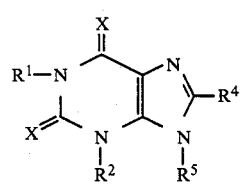

(II)

and their acid addition salts, wherein:

X is oxygen or sulfur;

$R^1$, $R^2$, $R^3$, $R^4$ and $R^5$ are selected from hydrogen; aliphatic hydrocarbons having 1-8 carbon atoms; cycloaliphatic hydrocarbons having 3-8 carbon atoms; substituted aliphatic hydrocarbons having 1-8 carbon atoms and cycloaliphatic hydrocarbons having 3-8 carbon atoms, substituted with 1-3 halogen atoms, $C_1$-$C_4$ alkyl, or hydroxy; alkoxy having 1-6 carbon atoms; phenyl; naphthyl; halo, hydroxy, or $C_1$-$C_4$ alkyl-substituted phenyl or naphthyl; phenoxy; substituted phenoxy; and the like, and acid addition salts thereof and further wherein at least one of $R^1$, $R^2$, $R^3$ or $R^5$ is other than hydrogen. For compound I, $R^1$, $R^2$ and $R^3$ are not each methyl simultaneously.

Suitable aliphatic hydrocarbon compounds include alkyl, alkenyl, alkynyl and the like.

Among the alkyl hydrocarbons are included methyl, ethyl, propyl, isopropyl, butyl, isobutyl, tert-butyl, pentyl, tert-pentyl, hexyl, heptyl, octyl, and the like.

Suitable alkenyl hydrocarbons are those having 2-8 carbon atoms and may include vinyl, allyl, isopropenyl, 1-propenyl, 2-butenyl, 3-pentenyl, 2-, 3-, or 4-hexenyl, and the like.

Suitable alkynyl hydrocarbons are those having 2-8 carbon atoms and may include ethynyl, 2-propynyl, 2-butynyl, 3-pentynyl, 3-hexynyl, 2-, 3-, or 4-heptynyl, and the like.

Suitable cylcoaliphatic groups include those having 3-8 carbon atoms, for example, cyclopentanyl, cycloheptanyl, cyclohexanyl, cyclopentenyl, cyclohexynyl, and the like, as well as lower alkyl, halo or hydroxy substituted alkoxy groups.

Suitable alkoxy groups include methoxy, ethoxy, butoxy, pentoxy, and the like.

Suitable aromatic groups include phenyl or naphthyl. Among the substituted aromatic groups are phenyl substituted in the ortho, meta, and/or para positions with lower alkyl groups having 1-4 carbon atoms, halogens, and hydroxy.

Where the compounds are intended as pesticides, the fluoride salts are generally excluded; where the compounds are intended as pestistate, caffeine is excluded.

The preparation and/or source for the compounds are well known, see Wells, J. N., et al., *J. Med. Chem.*, 24: 954-958 (1981); Kramer, G. I., et al., *Biochemistry*, Vol. 16, No. 15, pp. 3316-3321 (1977); Bruns, R. F., *Biochemical Pharmacology*, Vol. 30, pp. 325-333 (1981); and Garst, J. E., et al., *Journal of Medicinal Chemistry*, Vol. 19, No. 4, pp. 499-503 (1976).

Among the above-described xanthine derivatives, certain compounds have been shown to be especially effective. Thus, medium to large substitution in the 3-position ($R^2$) increases activity substantially. Further, substitution of small to medium (methyl, ethyl, propyl, i-propyl, butyl, isobutyl) groups in the 1-position ($R^1$) increases activity. Small to medium group substitution on the 7-position ($R^3$) also will enhance activity, as will certain small to medium group in the 8-position ($R^4$) However, chloro or bulky substituent in the 8-position ($R^4$) decreases activity as do certain substitutions in the 9-position ($R^5$).

The preferred compounds of the present invention are further defined as those compounds having a $V_{max}$ of more than 50% inhibition of feeding and an $EC_{50}$ of less than a 3% (gm/100 ml) concentration of spray. $V_{max}$ is expressed as the percent inhibition of feeding at the highest dose used (usually a 3% spray solution). $EC_{50}$ is the spray concentration (as calculated from dose-response curves) required to cause 50% inhibition of feeding. The lower the $EC_{50}$, the more effective the compound is in that less of the compound is required to achieve a 50% inhibition of feeding. Solvents for the compound include, for example, hydrocarbon solvents, such as isopropanol and methanol. Other solvents are known to those skilled in the art and may be used in the spray. The 3% (gm/100ml) concentration of spray is designed and limited by the solubility of the compound to be tested. Typically, above 3%, these compounds are insoluble in hydrocarbon solvents. Further, the 3% spray concentration is typically the maximum amount of active ingredient in a pesticidal or pestistatic composition; more typical is 1-2% concentration of active ingredient. *Pesticide Manufacturing and Toxic Materials Control Encyclopedia* (Noyes Data Corp. 1980).

Inhibition of feeding is determined at a time when untreated leaves show 20% of leaf area remaining. Calculation is then made by determining the percent leaf area remaining on leaves sprayed with drugs minus 20 divided by 80 (the maximal inhibition of feeding possible). The inhibition of feeding determination will be described in detail below. Basically, leaves are eaten by first-instar *Manduca sexta* which are placed at 6 per leaf.

In addition to *Manduca sexta*, other examples of insect species demonstrated to be affected by xanthine derivatives are Tenebrio (mealworm) larvae ($EC_{50}$ 0.1-0.3%); *Vanessa cardui* (painted lady butterfly) larvae ($EC_{50}$ 0.1-0.3%); *Oncopeltus fasciatus* (milkweed bug) nymph ($EC_{50}$ 0.3%); and, in solution, 1-methyl-3 isobutyl xanthine (IBMX) killed Culex (mosquito) larvae ($EC_{50}$ 0.007%). *Tribolium confusum* and *Tribolium castaneum* (flower beetle) adults were unaffected by IBMX doses up to 3%. However, in chronic tests, IBMX ($EC_{50}$ 0.2%) inhibited reproduction of these two species.

As mentioned above, in vertebrate tissues, methylxanthines are known to inhibit phosphodiesterase (PDE), enzymes which hydrolyze cAMP. Rall, T. W., *Pharmacological Bases of Therapeutics*, A. G. Gillman, L. Goodman, A. Gillman, Eds. (MacMillan, N.Y. 1980), p. 592; Sutherland, E. W., et al., *J. Biol. Chem.*, 232: 1077 (1958); and Butcher, R. W., et al., *J. Biol. Chem.*, 237: 1244 (1962). It was thus investigated as to whether xanthine derivatives could inhibit Manduca nerve cord PDE activity and, if so, whether the degree of such inhibition was related to observed pestistatic and pesticidal activity. The methodology for determining PDE inhibition is described below in Examples 8-11. These examples and FIG. 1D demonstrate the dose-dependent inhibition of nerve cord PDE activity by various xanthine derivatives whose inhibitory effects on leaf consumption are shown in Examples 4-7 and FIG. 1C.

Figure 1D:
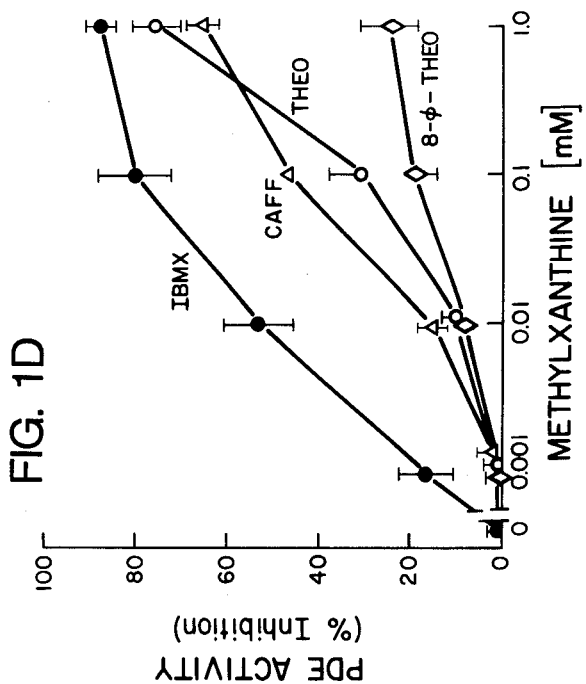
FIG. 1D is a graph showing the effect of the same xanthine derivatives on inhibiting cyclic AMP phosphodiesterase activity in homogenates of tobacco hornworm nerve cord.

The similarity of the graphs in FIGS. 1C and 1D demonstrates a strong correlation between PDE inhibition and pesticidal and pestistatic activity. This correlation is further evaluated in Examples 15 through 45 below. Based on the work to date, the most preferred compounds according to the present invention are those xanthine derivatives according to structural formulas (I) and (II) which also demonstrate a $K_i$ of 0.1 mM or less, wherein $K_i$ is defined as the concentration of xanthine derivative necessary to produce a 50% inhibition of enzyme activity for hornworm nerve cord PDE. Inhibition of phosphodiesterase activity for hornworm nerve cord for the purposes of determining $K_i$ within the meaning of this invention is determined in accordance with the methodology set out in Examples 8-11.

The pest-controlling agents of the present invention may be formulated as dusts, water dispersions, emulsions and solutions. They may comprise accessory agents such as dust carriers, solvents, emulsifiers, wetting and dispersing agents, stickers, deodorants, and masking agents (see, for example, *Encyclopedia of Chemical Technology*, Vol. 13, pp. 416 et seq.).

Dusts generally will contain low concentrations, 0.1–20%, of the compounds, although ground preparations may be used and diluted. Carriers commonly include sulfur, silicon oxides, lime, gypsum, talc, pyrophyllite, bentonite, kaolins, attapulgite, and volcanic ash. Selection of the carrier may be made on the basis of compatibility with the desired pest control composition (including pH, moisture content, and stability), particle size, abrasiveness, absorbability, density, wettability and cost. The agent of the invention, alone or in combination, and eluent is made by a variety of simple operations such as milling, solvent impregnations, fusing and grinding. Particle sizes usually range from 0.5–4.0 microns in diameter.

Wettable powders may be prepared by blending the agents of the invention in high concentrations, usually from 15–95%, with a dust carrier such as bentonite which wets and suspends properly in water. Twenty-two percent of a surface-active agent is usually added to improve the wetting and suspendability of the powder.

The pest-controlling agents may also be used in granules, which are pelleted mixtures of the agents, usually at 2.5–10%, and a dust carrier, e.g., adsorptive clay, bentonite or diatomaceous earth, and commonly within particle sizes of 250–590 microns. Granules may be prepared by impregnations of the carrier with a solution or slurry of the agents and may be used principally for mosquito larvae treatment or soil applications.

The agent may also be applied in the form of an emulsion, which comprises a solution of the agents in water-immiscible organic solvents, commonly at 15–50%, with a few percent of surface active agent to promote emulsification, wetting, and spreading. The choice of solvent is predicated upon solubility, safety to plants and animals, volatility, flammability, compatibility, odor and cost. The most commonly used solvents are kerosene, xylenes, and related petroleum fractions, methylisobutylketone, and amyl acetate. Water emulsion sprays from such emulsive concentrates may be used for plant protection and for household insect control.

The agents may also be mixed with baits, usually comprising 1–5% of agents with a carrier especially attractive to insects. Carriers include sugar for houseflies, protein hydrolysate for fruit flies, bran for grasshoppers, and honey, chocolate, or peanut butter for ants.

The agents may be included in slow release formulations which incorporate non-persistent compounds, insect growth regulators and sex pheromones in a variety of granular microencapsulated and hollow fiber preparations.

The pest-controlling agents of the present invention may be applied depending on the properties of the particular pest-controlling compound, the habits of the pest to be controlled, and the site of the application to be made. It may be applied by spraying, dusting or fumigation.

Doses of the weight of the ingredients may typically vary between 0.001 and 100 pounds/acre, preferably between 0.001–5 pounds/acre.

Sprays are the most common means of application and generally will involve the use of water as the principal carrier, although volatile oils may also be used. The pest-controlling agents of the invention may be used in dilute sprays (e.g., 0.001–10%) or in concentrate sprays in which the composition is contained at 10–98%, and the amount of carrier to be applied is quite reduced. The use of concentrate and ultra-low volume sprays will allow the use of atomizing nozzles producing droplets of 30–80 microns in diameter. Spraying may be carried out by airplane or helicopter.

Aerosols may also be used to apply the pest-controlling agents. These are particularly preferred as space sprays for application to enclosures, particularly against flying insects. Aerosols are applied by atomizing amounts of liquified gas dispersion or bomb, but can be generated on a larger scale by rotary atomizers or twin-fluid atomizers. Carriers used as aerosols or liquified gas may include mineral spirits, ethanol, isopropanol, deionized water, and hydrocarbon propellants, such as isobutane, n-butane, and propane or nonflammable fluorinated hydrocarbon propellants, or compressed gases, such as nitrogen, carbon dioxide, or nitrous oxide. The aerosol composition will typically comprise 0.001–10% pest-controlling agents of this invention, more typically 0.05–3%, and the remainder being aerosol or liquified gas ingredients. *The Science and Technology of Aerosol Packaging* (John Wiley & Sons 1974).

A simple means of pest-controlling agent dispersal is by dusting. The pest-controlling agent is applied by introducing a finely divided carrier with particles typically of 0.5–3 microns in diameter into a moving air stream.

Having now generally described the invention, the same will become better understood by reference to certain specific examples which are included herein for purposes of illustration only and are not intended to be limiting unless otherwise specified.

EXAMPLE 1

Various concentrations of finely powdered tea leaves or powdered coffee beans were mixed in artificial media which was then plated out in small petri dishes and allowed to harden. At concentrations from 0.3–10% (wt/wt) for coffee and from 0.1–3% for tea, larvae of *Manduca sexta* (tobacco hornworm) housed in these dishes showed a dose-dependent inhibition of feeding associated with hyperactivity, tremors and stunted growth. At concentrations greater than 10% (for coffee) or 3% (for tea), larvae were killed within 24 hours.

EXAMPLE 2

Figure 1A:
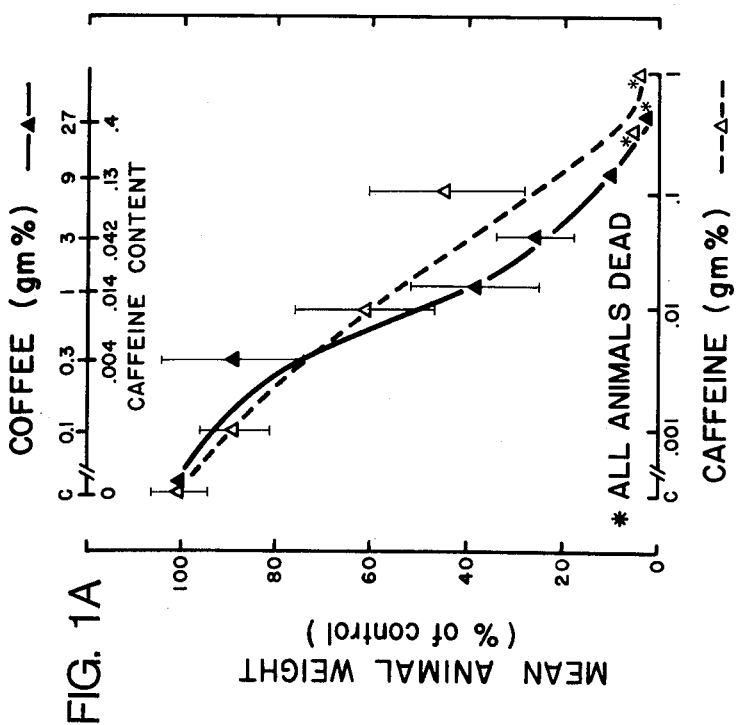
FIG. 1A shows the effect on tobacco hornworm body weight of powdered coffee beans or caffeine incorporated into artificial media.

The larvae of *Manduca sexta* were fed on either artificial or natural food. When added to artificial media, caffeine (the major methylxanthine found in tea and coffee) exerted behavioral effects that were qualitatively similar to those of the tea and coffee described above. In addition, as FIG. 1A shows, the concentration of purified caffeine required for 50% inhibition of weight gain was nearly identical to the endogenous caffeine content of the coffee-media mixture which caused 50% inhibition of weight gain. Further, the dried tea leaves, which contain 2–3 times the caffeine content of dried coffee beans, were about 2–3 times as effective as coffee beans in inhibiting weight gain. Further, the concentrations of caffeine which are found naturally in undried tea leaves (0.68–2.1%) or coffee beans (0.8–1.8%) were sufficient to kill most *Manduca*

*larvae*. Thus, caffeine functions as an endogenous insecticide.

EXAMPLE 3

Figure 1B:
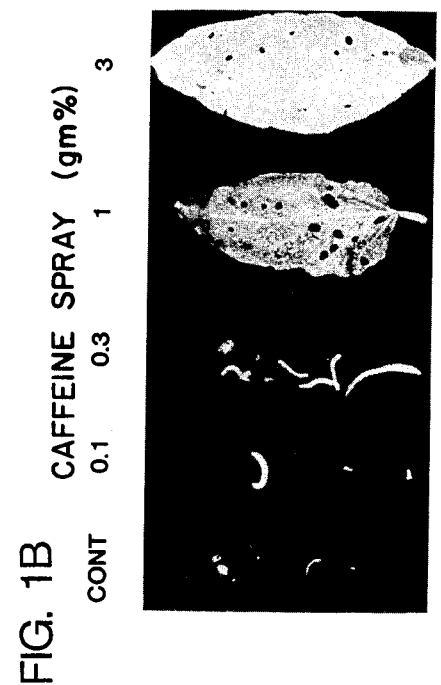
FIG. 1B shows the dose-dependent antifeeding effect of caffeine.

Various xanthine derivatives were tested on natural feeding substrates, such as tomato leaves, the xanthine derivatives being those compounds wherein at least one of $R^1$, $R^2$, $R^3$, and $R^5$ are other than hydrogen. The compounds, applied as a spray, exerted pestistatic and pesticidal effects which resulted in leaf protection. FIG. 1B shows a typical result for caffeine.

EXAMPLES 4–7

FIG. 1C (which quantitates the amount of leaf remaining) summarizes the dose-response curves for caffeine (Example 4), theophylline (Example 5), and the synthetic compound, 1-methyl- 3-isobutylxanthine (IBMX) (Example 6). In Example 3 above and each of Examples 4–6, isolated hydrated tomatoe leaves were pre-sprayed with the compound(s) or vehicle (usually MeOH) at the concentration shown, allowed to dry and placed in closed plexiglass containers. A group of six, three-day old tobacco hornworm larvae (initially reared on artificial media) were then placed on each leaf, and the amount of leaf remaining was measured at the end of four days. Values shown are the mean (±SEM) of three separate experiments. FIG. 1C also shows the relatively weak effects of 8-phenyltheophylline (Example 7), a known adenosine receptor blocker (Daly, J. W., *J. Med. Chem.*, 25: 197 (1982)).

EXAMPLES 8–11

Nerve cord was dissected from 40–60 mm long *M. sexta* larvae, cleaned, and homogenized (2 mg/ml) in 6 Mm Tris-maleate, pH 7.4. PDE activity was measured (4 min. incubation at 30° C.) in an assay system (0.1 ml) containing 80 mM Tris-maleate, pH 7.4; 6 mM Mg—$SO_4$; $10^{-7}$ $M^3H$-cyclic AMP; and tissue homogenate (0.02 ml). Nerve cord was evaluated in the presence and the absence of the xanthine derivative. For purposes of the evaluation, the rate of formation of $^3H$-5' AMP was measured using the technique described in Filburn, C. R., *Anal. Biochem.*, 52: 505 (1973). Under these conditions, enzyme activity was linear with respect to time and enzyme concentration. The values shown in FIG. 1D are the mean (±SEM) of three separate experiments. As may be seen, the patterns of activity in the two graphs are quite similar.

EXAMPLE 12

To determine if the dosage of xanthine derivatives described in experiments 4, 7 and 8–11 and ingested by the larvae (causing pestistatic and pesticidal activity in vivo) were actually absorbed by the animals and were sufficient to inhibit PDE in vitro, additional experiments were carried out in order to estimate tissue levels of xanthine derivative following three days of feeding on various doses of the derivative. Groups of six larvae were placed on leaves treated with vehicle or theophylline spray. After three days, leaf area was recorded and larvae (alive or dead) were rinsed to remove any compound adhering to their cuticle, homogenized whole, centrifuged, and the cell-free supernatant assayed for theophylline content by immunoenzymatic assay (Emit-AAD theophylline assay (Syva Company, Palo Alto, CA.)). This particular assay shows little cross-reactivity with theophylline metabolites. From mammalian studies, it is known that theophylline penetrates freely into all body compartments (Rall, T. W., supra.). Larvae feeding on leaves treated with a 1% spray (an amount causing about 50% inhibition of·leaf consumption) were found to contain an internal theophylline concentration of 4.1±1.1 mM (mean ±deviation for two groups of six pooled animals). This concentration was sufficient to cause more than an 80% inhibition of hornworm nerve cord PDE activity in vitro. This observation tends to rule out the hypothesis wherein adenosine receptors are involved as a mechanism for the antifeeding effects of the xanthine derivatives, since, in vertebrates, xanthine derivatives such as theophylline are competitive adenosine receptor antagonists, but exert such antagonism at much lower concentrations, typically 1–25 micromoles. See Bruns, R., *et al., Proc. Natl. Acad. Sci. USA,* 77: 5547 (1980); Williams, M., *et al., Proc. Natl. Acad. Sci. USA,* 77: 6892 (1980).

EXAMPLE 13

Xanthine derivatives have been reported to have calcium mobilizing effects (Links, J. R., et al., *Circ. Res.,* 30: 367 (1972)). Xanthine derivatives are known to mobilize calcium from sarcoplasmic reticulum, an effect which is blocked by diltiazem or procaine. IBMX was evaluated with regard to antifeeding effects in the presence of both diltiazem and procaine, neither reversing the observed antifeeding effects.

EXAMPLE 14

Xanthine derivatives have also been reported to affect calcium movement across the plasma membrane (Links, J. R., et al., supra; Saeki, K., et al., *Life Sci.,* 32: 2973 (1983)). The pestistatic and pesticidal effects of IBMX were evaluated in the presence of D600, verapamil, and nimodipine, compounds which are known to block plasma membrane calcium channels. The pestistatic and pesticidal effects of IBMX appeared unaffected by these compounds.

Discussion

Whereas caffeine has been reported to be 10-fold weaker than theophylline as an adenosine antagonist (Bruns, R., et al., supra), as demonstrated by the above Examples, caffeine was somewhat more potent than theophylline in preventing leaf eating and about equally potent as a PDE inhibitor. See FIGS. 1C and 1D. Also, whereas IBMX and theophylline are roughly equally potent in blocking adenosine receptors (Bruns, R., et al., supra) IBMX was about 10-fold more potent both in disruption of feeding and in PDE inhibition. See FIG. 1D. Furthermore, the very potent adenosine antagonist, 8-phenyltheophylline, ($K_i$ for adenosine receptor (0.12–1.0 micromoles) (Daly, J. W., *J. Med. Chem.,* 25: 197 (1982); Bruns, R., et al., supra) exerted little antifeeding effect and was a very weak PDE inhibitor (see FIGS. 1C and 1D). Additionally, the non-xanthine, papavarine, was a potent inhibitor both of insect PDE ($K_i$=40 micromoles) and of the ability of Manducca to feed ($EC_{50}$=0.1% spray). Unlike xanthine derivatives, papavarine is an inhibitor of adenosine uptake, and it potentiates, rather than blocks physiological effects on adenosine receptors (Huang, M., et al., *Life Sci.,* 14: 489 (1974)). Taken together, these data are more consistent with a mechanism of action related to PDE inhibition than to adenosine blockade.

Cumulatively, these data suggest that pestistatic and pesticidal effects of the xanthine derivatives are mediated through an alteration of tissue cyclic AMP levels, most likely secondarily to an inhibition of phosphodiesterase. Thus, the naturally occurring xanthine derivatives function as endogenous pest-controlling agents.

EXAMPLE 15–45

Thirty-one compounds conforming to the general formula (I) or (II) above were prepared or obtained and evaluated with regard to pesticidal and pestistatic activity. The results of the evaluation are reported in Table 1 below. In Table 1 below, $EC_{50}$ and $V_{max}$ are as described above, with active compounds being those compounds with a $V_{max}$ of more than 50% inhibition of feeding and an $EC_{50}$ of less than 3% (gm/100 ml) concentration of spray. As may be seen from Table 1, Examples 15–31 are active compounds within the above meaning, with Examples 32–44 being inactive compounds. Example 45 is weakly active. Of the seventeen active compounds, twelve are more active than caffeine (1,3,7-trimethylxanthine), Examples 16–21, 24, 26, and 28–31.

TABLE 1
STRUCTURAL-ACTIVITY RELATIONSHIPS OF XANTHINES WITH PESTICIDAL ACTIVITY

| Ex. | Compound | $EC_{50}$ | $V_{max}$ |
|---|---|---|---|
| Active Compounds | | | |
| 15 | 1,3-dimethyl-xanthine (theophylline) | 1.5 | 94 |
| 16 | 1,3-diethyl-xanthine | 0.33 | 98 |
| 17 | 1,3-dipropyl-xanthine | 0.035 | 95 |
| 18 | 1,3-diallyl-xanthine | 0.35 | 99 |
| 19 | 1,3-dibenzyl-xanthine | 0.45 | 70 |
| 20 | 1-methyl,3-isobutyl-xanthine | 0.3 | 95 |
| 21 | 1-isoamyl,3-isobutyl-xanthine | 0.2 | >52 |
| 22 | 1-phenethyl,3-ethyl-xanthine | 0.6 | 96 |
| 23 | 1,3,7-trimethyl-xanthine (caffeine) | 0.3 | 98 |
| 24 | 1,3-dimethyl,7-(2-chlorethyl)-xanthine | 0.3 | 95 |
| 25 | 1,3-dimethyl,7-(beta-hydroxypropyl-xanthine) | 1.5 | 95 |
| 26 | 1,3,7-trimethyl,8-methoxy-xanthine | 0.5 | 86 |
| 27 | 3,7-dimethyl-xanthine (theobromine) | 1.0 | 87 |
| 28 | 1,3-dipropyl,7-methyl-xanthine | 0.48 | 84 |
| 29 | 1,3,7-tripropyl-xanthine | 0.19 | 95 |
| 30 | 1,3-dipropyl,7-benzyl-xanthine | 0.08 | 96 |
| 31 | 1,3-dibutyl-xanthine | 0.044 | 90 |
| Inactive Compounds | | | |
| 32 | xanthine | >3 | 0 |
| 33 | 1-methyl-xanthine | >3 | 21 |
| 34 | 3-methyl-xanthine | >3 | 8 |
| 35 | 7-methyl-xanthine | >3 | 29 |
| 36 | 8-methyl-xanthine | >3 | 35 |
| 37 | 9-methyl-xanthine | >3 | 10 |
| 38 | 1,7-dimethyl-xanthine | >3 | 30 |
| 39 | 1,7-dimethyl-uric acid | >3 | 30 |
| 40 | 1,3,7-trimethyl-uric acid | >3 | 40 |
| 41 | 1,3-dimethyl-7-acetyl-xanthine | >3 | 18 |
| 42 | 1,3-dimethyl-8-phenyl-xanthine | >3 | 38 |
| 43 | 1,3-dipropyl-8-phenyl-xanthine | >3 | 0 |
| 44 | 1,3,7-trimethyl-8-chloro-xanthine | >3 | 40 |
| Weakly Active | | | |
| 45 | 1,3,9-trimethyl-xanthine | >3 | 50 |

EXAMPLE 46

Figure 2:
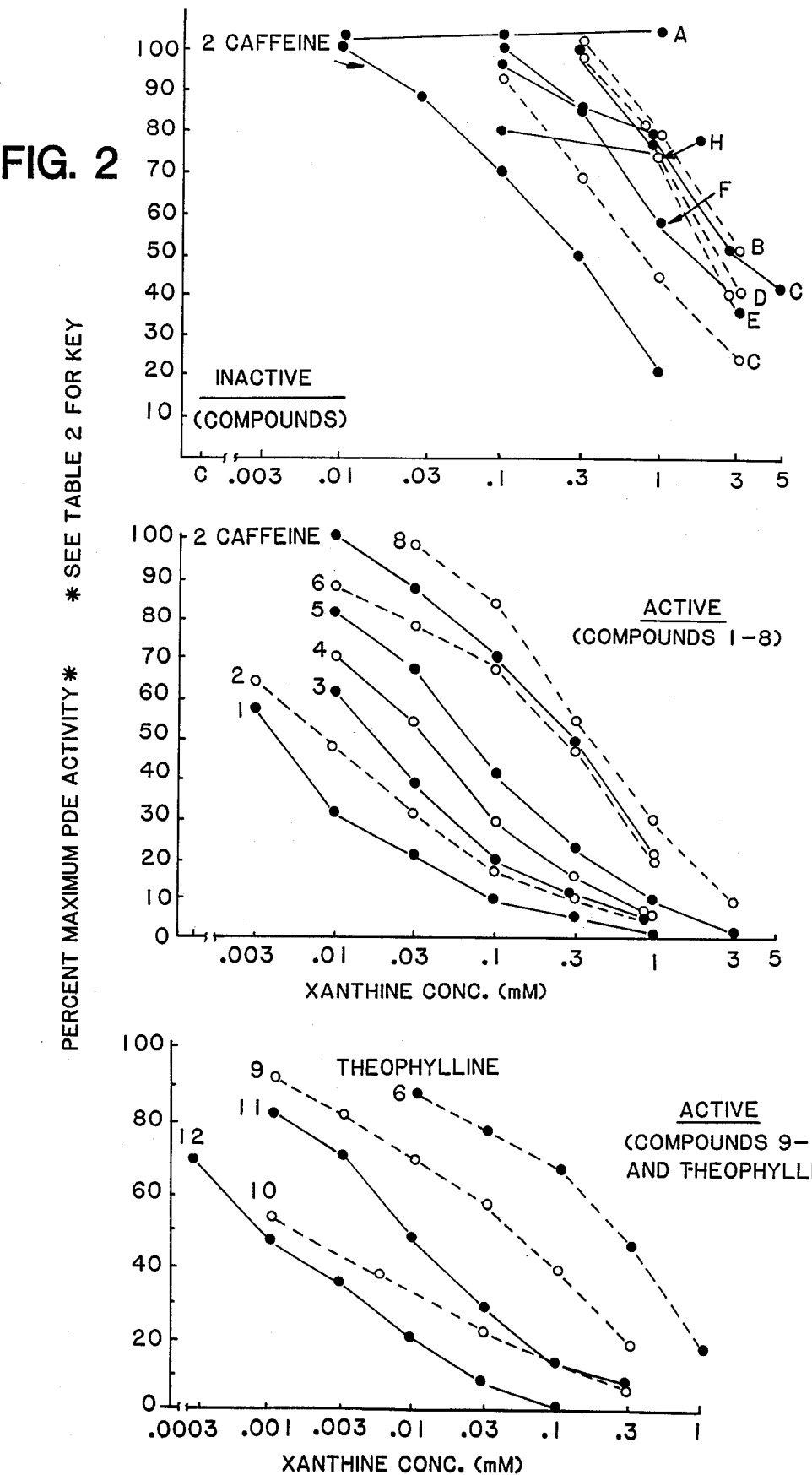
FIG. 2 is a graph showing the phosphodiesterase inhibiting activity of various xanthine derivatives in tobacco hornworm nerve cord.

Fifteen xanthine derivatives, and xanthine itself, were evaluated according to their ability to inhibit phosphodiesterase activity in hornworm nerve cord using the methodology set out in Examples 8–11 above. The sixteen compounds and the identifying key for FIG. 2 appear in Table 2 below. As may be seen from FIG. 2, compounds 1–5 have a $K_i$ ($K_i$, as defined above, being the concentration in mM necessary to cause a 50% inhibition in PDE activity) of 0.1 or less. These same five compounds have a $V_{max}$ of at least 95 and an $EC_{50}$ of 0.33 or less.

TABLE 2
KEY FOR GRAPH OF FIG. 2

| | |
|---|---|
| Inactive Compounds | |
| A. | 1,3-dimethyl-7-acetyl-xanthine |
| B. | 1-methyl-xanthine |
| C. | 8-methyl-xanthine |
| D. | xanthine |
| E. | 7-methyl-xanthine |
| F. | 3-methyl-xanthine |
| G. | 1,3-dimethyl-8-chloro-xanthine |
| H. | 1,3-dimethyl-8-phenyl-xanthine |
| Active Compounds | |
| 1. | 1,3-dipropyl-xanthine |
| 2. | 1-methyl,3-isobutyl-xanthine |
| 3. | 1,3-diallyl-xanthine |
| 4. | 1,3-diethyl-xanthine |
| 5. | 1,3-dimethyl-7-(2-chlorethyl)-xanthine |
| 6. | 1,3-dimethyl-xanthine (theophylline) |
| 7. | 1,3,7-trimethyl-xanthine (caffeine) |
| 8. | 1,3-dimethyl-7-(beta-hydroxypropyl)-xanthine |
| 9. | 1,3-dipropyl,7-methyl-xanthine |
| 10. | 1,3,7-tripropyl-xanthine |
| 11. | 1,3-dipropyl,7-benzyl-xanthine |
| 12. | 1,3-dibutyl-xanthine |

This strong correlation between in vitro PDE inhibition and pesticidal activity allows one to accurately predict the pesticidal activity of xanthine derivatives based on PDE inhibition in tobacco hornworm nerve cord.

EXAMPLE 47

These four structurally similar compounds were tested as described in Example 46: 1,3,7-trimethylxanthine (caffeine); 1,7-dimethyl-xanthine; 1,3,9-tri-methyl-xanthine; and 1,3-dimethyl-xanthine.

The caffeine compound tested according to the methods disclosed in the present invention is active. Therefore, one would predict that the above three compounds which differ only by a single methyl group would also be active. However, the tests show that only 1,3-dimethyl-xanthine was active. 1,7-dimethylxanthine was inactive and 1,3,9-trimethyl-xanthine was only weakly active. These results are not obvious and one could only predict them by knowing the teachings of the application. More specifically, the inventor's in vitro phosphodiesterase testing procedure correctly predicts as shown in Examples 15–45 that, of the three compounds, only 1,3-dimethyl-xanthine is active. Thus, as a result of the present invention, it is possible to quickly and routinely evaluate, in vitro, potentially active compounds based on their ability to inhibit phosphodiesterase activity.

Having now fully described this invention, it will be understood by those of skill in the art that the same may be performed within a wide and equivalent range of compositions, parameters, structures, modes of application, pests, formulations, and ranges without affecting the scope of the invention or any embodiment thereof.

What is claimed and desired to be covered by letters patent is:

1. A method of controlling a phosphodiesterase-containing invertebrate pest which comprises bringing into contact with said pest a pest-controlling amount of a xanthine derivative having the general formula:

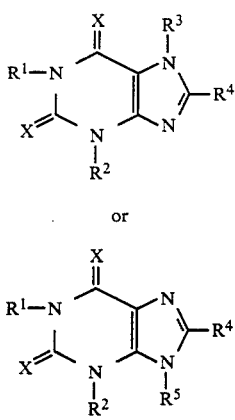

I or

II or the acid addition salts thereof, wherein
X is oxygen or sulfur; and
$R^1$, $R^2$, $R^3$, $R^4$ and $R^5$ are selected from hydrogen; aliphatic hydrocarbons having 1-8 carbon atoms and cycloaliphatic hydrocarbons having 3-8 carbon atoms; aliphatic hydrocarbons having 1-8 carbon atoms and cycloaliphatic hydrocarbons having 3-8 carbon atoms substituted with 1-3 halogen atoms, $C_1$-$C_4$ alkyl, or hydroxy; alkoxy having 1-6 carbon atoms; phenyl; naphthyl; halo, hydroxy, or $C_1$-$C_4$ alkyl-substituted phenyl or naphthyl; or phenoxy;

with the proviso that for compound I, at least one of $R^1$, $R^2$, $R^3$ and $R^4$ is other than hydrogen, methyl and ethyl, and with the further proviso that said compound has a $V_{max}$ of more than 50 and an $EC_{50}$ of no more than 3, where $V_{max}$ is expressed as the percent inhibition of feeding at a 3% (gm/100 ml) concentration of spray and $EC_{50}$ is defined as the spray concentration (gm/100 ml) required to cause a 50% inhibition of feeding.

2. A method of inhibiting the feeding of a phosphodiesterase-containing invertebrate pest which comprises bringing into contact with said pest a feed-inhibiting amount of a xanthine derivative having the general formula:

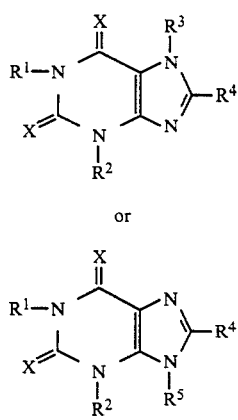

I or

II or the non-hydrogen fluoride acid addition salts thereof, wherein
X is oxygen or sulfur; and
$R^1$, $R^2$, $R^3$, $R^4$ and $R^5$ are selected from hydrogen; aliphatic hydrocarbons having 1-8 carbon atoms and cycloaliphatic hydrocarbons having 3-8 carbon atoms; aliphatic hydrocarbons having 1-8 carbon atoms and cycloaliphatic hydrocarbons having 3-8 carbon atoms, substituted with 1-3 halogen atoms, $C_1$-$C_4$ alkyl, or hydroxy; alkoxy having 1-6 carbon atoms; phenyl or naphthyl; halo, hydroxy, or $C_1$-$C_4$ alkyl-substituted phenyl or naphthyl; or phenoxy;

with the proviso that for compound I, at least one of $R^1$, $R^2$, $R^3$ and R4 is other than hydrogen, methyl and ethyl; and with the further proviso that, said compound has a $V_{max}$ of more than 50 and an $EC_{50}$ of no more than 3, where $V_{max}$ is expressed as the percent inhibition of feeding at a 3% (gm/100 ml) concentration of spray and $EC_{50}$ is defined as the spray concentration (gm/100 ml) required to cause a 50% inhibition of feeding.

3. The method of claim 1, wherein said xanthine derivative is selected from the group consisting of 1,3-dipropylxanthine; 1,3-diallyl-xanthine; 1,3-dibenzyl-xanthine; 1-methyl-3-isobutyl-xanthine; 1-isoamyl-3-isobutyl-xanthine; 1-phenethyl-3-ethyl-xanthine; 1,3-dimethyl-7-(2-chloroethy-1)-xanthine; 1,3-dimethyl-7-beta-hydroxypropyl)-xanthine; 1,3,7-trimethyl-8-methoxy-xanthine; 1,3-dipropyl-7-methyl-xanthine; 1,3,7-tripropyl-xanthine; 1,3-dipropyl-7-benzyl-xanthine; and 1,3-dibutyl-xanthine.

4. The method of claim 2, wherein said xanthine derivative is selected from the group consisting of 1,3-dipropyl-xanthine; 1,3-diallyl-xanthine; 1,3-dibenzyl-xanthine; 1-methyl-3-isobutyl-xanthine; 1-isoamyl-3-isobutyl-xanthine; 1-phenethyl-3-ethyl-xanthine; 1,3-dimethyl-7-(2-chloroethyl)-xanthine; 1,3-dimethyl-7-beta-hydroxypropyl)-xanthine; 1,3,7-trimethyl-8-methoxy-xanthine; 1,3-dipropyl-7-methyl-xanthine; 1,3,7-tripropyl-xanthine; 1,3-dipropyl-7-benzyl-xanthine; and 1,3-dibutyl-xanthine.

5. The method of claim 1, wherein said xanthine derivative is selected from the group consisting of 1,3-dipropylxanthine, 1,3,7-tripropylxanthine, 1,3-dipropyl-7-benzylxanthine, 1,3-dibutylxanthine and 1-methyl-3-isobutylxanthine.

6. The method of claim 2, wherein said xanthine derivative is selected from the group consisting of 1,3dipropylxanthine, 1,3,7-tripropylxanthine, 1,3-dipropyl-7-benzylxanthine, 1,3-dibutylxanthine and 1-methyl-3isobutylxanthine.

7. The method of claims 1 or 2 wherein said xanthine derivative is 1,3-dipropyl-xanthine.

8. The method of claim 1 wherein said xanthine derivative has a $K_i$ of not greater than 0.1, where $K_i$ is defined as the concentration in mM of said xanthine derivative required to produce a 50% inhibition of enzyme activity for hornworm nerve cord phosphodiesterase.

9. The method of claim 2 wherein said xanthine derivative has a $K_i$ of not greater than 0.1, where $K_i$ is defined as the concentration in mM of said xanthine derivative required to produce a 50% inhibition of enzyme activity for hornworm nerve cord phosphodiesterase.

10. A composition useful for controlling a phosphodiesterase-containing invertebrate pest comprising the following ingredients:
(1) a pest-controlling amount of an agent selected from xanthine derivatives having the general formula:

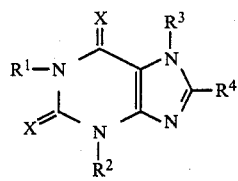

I or

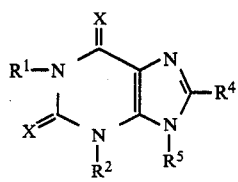

II or the acid addition salts thereof, wherein
X is oxygen or sulfur; and
$R_1$, $R_2$, $R_3$, $R_4$ and $R_5$ are selected from hydrogen; aliphatic hydrocarbons having 1-8 carbon atoms and cycloaliphatic hydrocarbons having 3-8 carbon atoms; aliphatic hydrocarbons having 1-8 carbon atoms and cycloaliphatic hydrocarbons having 3-8 carbon atoms, substituted with 1-3 halogen atoms, $C_1$-$C_4$ alkyl, or hydroxy; alkoxy having 1-6 carbon atoms; phenyl; naphthyl; halo, hydroxy, or $C_1$-$C_4$ alkyl-substituted phenyl or naphthyl; or phenoxy;
with the proviso that for compound I, at least one of $R^1$, $R^2$, $R^3$ and $R^4$ is other than hydrogen, methyl and ethyl, and
with the further proviso that, said compound has a $V_{max}$ of more than 50 and an $EC_{50}$ of no more than 3, where $V_{max}$ is expressed as the percent inhibition of feeding at a 3% (gm/100 ml) concentration of spray and $EC_{50}$ is defined as the spray concentration (gm/100 ml) required to cause a 50% inhibition of feeding together with a dust carrier; and
(2) a carrier selected from a dust carrier, a granule or pellet carrier form, a liquid form or an aerosol.

11. The composition of claim 10, wherein said xanthine derivative is selected from the group consisting of 1,3-dipropyl-xanthine; 1,3-diallyl-xanthine; 1,3-dibenzylxanthine; 1-methyl-3-isobutyl-xanthine; 1-isoamyl-3-isobutylxanthine; 1-phenethyl-3-ethyl-xanthine; 1,3-dimethyl,7-(2-chloroethyl)-xanthine; 1,3-dimethyl-7-beta-hydroxypropyl)-xanthine; 1,3,7-trimethyl-8-methoxy-xanthine; 1,3-dipropyl-7-methyl-xanthine; 1,3,7-tripropyl-xanthine; 1,3-dipropyl-7-benzyl-xanthine; and 1,3-dibutyl-xanthine.

12. The method of claim 10, wherein said xanthine derivative is selected from the group consisting of 1,3dipropylxanthine, 1,3,7-tripropylxanthine, 1,3-dipropyl-7-benzylxanthine, 1,3-dibutylxanthine and 1-methyl-3-isobutylxanthine.

13. The composition of claim 10 wherein said carrier is a dust carrier.

14. The composition of claim 13 wherein said dust carrier is selected from the group consisting of sulfur, silicon oxides, lime, gypsum, talc, pyrophyllite, bentonite, kaolin, attapulgite, and volcanic ash.

15. The composition of claim 10 wherein said carrier is granule or pellet, carrier form.

16. The composition of claim 15 wherein said granule- or- pellet-forming carrier is selected from the group consisting of sulfur, silicon oxides, lime, gypsum, talc, pyrophyllite, bentonite, kaolin, attapulgite and volcanic ash.

17. The composition of claim 10 wherein said carrier is an aerosol

18. The composition of claim 10 wherein said carrier is a liquid.

* * * * *